United States Patent
Saurer et al.

[11] Patent Number: 5,818,341
[45] Date of Patent: Oct. 6, 1998

[54] ULTRASONIC DEVICE IN PARTICULAR FOR DETECTING THE PRESENCE OF FOREIGN BODIES ON THE SURFACE OF A WINDOW

[75] Inventors: Eric Saurer, Bevaix; Roland Jeanmonod, Neuchâtel, both of Switzerland

[73] Assignee: Asulab S.A., Bienne, Switzerland

[21] Appl. No.: 848,428

[22] Filed: May 8, 1997

[30] Foreign Application Priority Data

May 30, 1996 [FR] France ............................. 96 06669

[51] Int. Cl.⁶ .................................................. G08B 21/00
[52] U.S. Cl. .......................... 340/602; 367/93; 367/140; 318/483
[58] Field of Search .................... 347/602; 318/483, 318/460; 367/93, 140

[56] References Cited

U.S. PATENT DOCUMENTS

| | | | |
|---|---|---|---|
| 5,203,207 | 4/1993 | Sugiyama | 340/602 |
| 5,432,415 | 7/1995 | Ittah et al. | 318/483 |
| 5,436,060 | 7/1995 | Saurer et al. | 428/195 |
| 5,598,380 | 1/1997 | Saurer et al. | 367/140 |

FOREIGN PATENT DOCUMENTS 0 512 653   11/1992   European Pat. Off. .
0 638 822    2/1995   European Pat. Off. .

*Primary Examiner*—Edward Lefkowitz
*Attorney, Agent, or Firm*—Griffin, Butler, Whisenhunt & Szipl, LLP

[57] ABSTRACT

The invention concerns an ultrasonic detection device intended to detect the presence of foreign bodies, on the surface of a window comprising a first sheet having a first thickness, comprising a transducer co-operating with a first face of said first sheet, said transducer being able to emit an ultrasonic signal of frequency $f_t$ and also able to receive a reflected ultrasonic signal on a second face of the first sheet, the variation in said reflected signal being representative of the presence or absence of foreign bodies on said second face facing said transducer. This device is characterized in that the frequency $f_t$ is selected to satisfy the following equation:

$$f_K/100 \leq |f_t - f_K| \leq f_K/10$$

where $f_K = K \cdot V/2e$ is the frequency of the Kth natural mode of the resonant cavity formed by the first sheet of glass, K being a non zero integral number, V the speed of propagation of the ultrasonic wave in the material forming the first sheet and e the thickness of the first sheet.

4 Claims, 3 Drawing Sheets

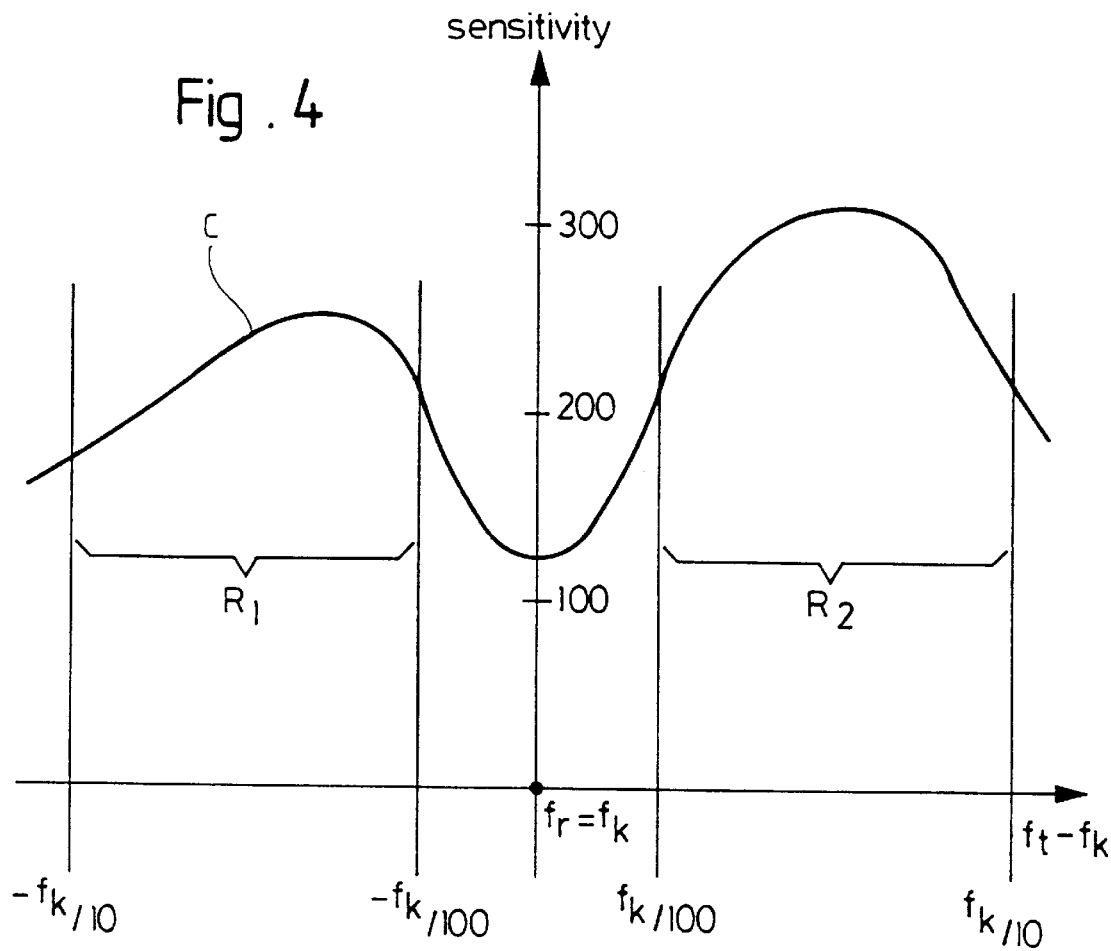

ULTRASONIC DEVICE IN PARTICULAR FOR DETECTING THE PRESENCE OF FOREIGN BODIES ON THE SURFACE OF A WINDOW

The invention concerns an ultrasonic device for detecting the presence of foreign bodies, in particular moist bodies, present on the surface of a window or a windscreen comprising at least a first sheet having a first thickness, the device comprising a transducer co-operating with a first face of said first sheet, said transducer being able to emit an ultrasonic signal of frequency $f_t$ and also being able to receive an ultrasonic signal reflected onto a second face of the first sheet, the variation in the reflected signal being representative of the presence or absence of foreign bodies on said second face facing said transducer.

A device of this type is already disclosed in patent document EP 0 512 653, in an application to the automatic control of a windscreen wiper device intended for removing foreign bodies such as water on the surface of a windscreen.

Furthermore, patent document EP-A-0 641 696 proposes a window comprising such an ultrasonic device for detecting the presence of foreign bodies on one of its faces. In this document, it is specified that in order to obtain optimum sensitivity to detection of foreign bodies present on the surface of a sheet of glass to which a transducer is connected, the amplitude of the vibration of this sheet of glass must be maximum. This condition is only achieved if the frequency of one of the resonance modes of the resonant cavity formed by the sheet of glass in question is substantially equal to the frequency of the ultrasonic wave emitted by the transducer. In other words, the transducer frequency $f_t$ must be substantially equal to the frequency $f_k$ of one of the resonance modes of the sheet, according to the equation $f_k = K.V/2e$, V being the speed of the wave in the material forming the sheet, e being the thickness of said sheet, K being a non zero integral number and $f_t$ being the resonant frequency of the transducer free of any stress, i.e. in particular when it is not connected to the sheet.

It is thus understood that it is easy to select a transducer emitting an ultrasonic wave whose frequency is adapted to the thickness of the sheet of glass of the windscreen in contact with the exterior environment and in particular rain when one wishes to use this device to start a windscreen wiper device as described in patent document EP-A-0 512 653.

The solution disclosed in patent document EP-A-0 641 696 is satisfactory but the sensitivity of the detection device may be further improved, in particular in the case of the presence of a very small quantity of elements to be detected.

A main aim of the invention is thus to improve the solutions of the prior art by providing a device for ultrasonically detecting foreign bodies, which has even better detection sensitivity.

The invention thus concerns an ultrasonic detection device intended to detect the presence of foreign bodies, in particular moist bodies, present on the surface of a window comprising at least a first sheet, having a first thickness, the device comprising a transducer co-operating with a first face of said first sheet, said transducer being able to emit an ultrasonic signal of frequency $f_t$ and also being able to receive an ultrasonic signal reflected onto a second face of the first sheet, the variation in the reflected signal being representative of the presence or absence of foreign bodies on said second face facing said transducer, characterized in that frequency $f_t$ is selected to satisfy the following equation:

$$f_K/100 \leq |f_t - f_K| < f_K/10$$

where $f_K = K.V/2e$ is the frequency of the kth natural mode of the resonant cavity formed by the first sheet of glass, K being a non zero integral number, V the speed of propagation of the ultrasonic wave in the material forming the first sheet, and e the thickness of the first sheet.

The invention thus enables selection of the resonant frequency of the ultrasonic transducer which, when the transducer is fixed onto a sheet of glass acting as resonant cavity for the ultrasonic wave emitted by said transducer, is such that the sensitivity to a slight disturbance created at the surface of said sheet of glass is optimum.

According to a preferred embodiment of the invention, transducer frequency $f_t$ is selected to satisfy the following equation:

$$f_K/100 \leq f_t - f_K \leq f_K/10,$$

$f_t$ being greater than $f_K$.

Other characteristics and advantages of the invention will appear more clearly upon reading the following description of an embodiment of the invention given purely by way of illustrative and non-limiting example, said description being given in conjunction with the drawings in which:

FIG. 4 is a curve of the detection sensitivity to the presence of a drop of water, whose surface in contact with the windscreen is precisely determined, on the surface of the windscreen, expressed in arbitrary units, as a function of the frequency difference $f_t - f_K$.

The description of the invention will be made within the framework of an application for the elimination of moist foreign bodies such as rain, snow, mud, etc. present on the surface of a motor vehicle windscreen.

Figure 1:
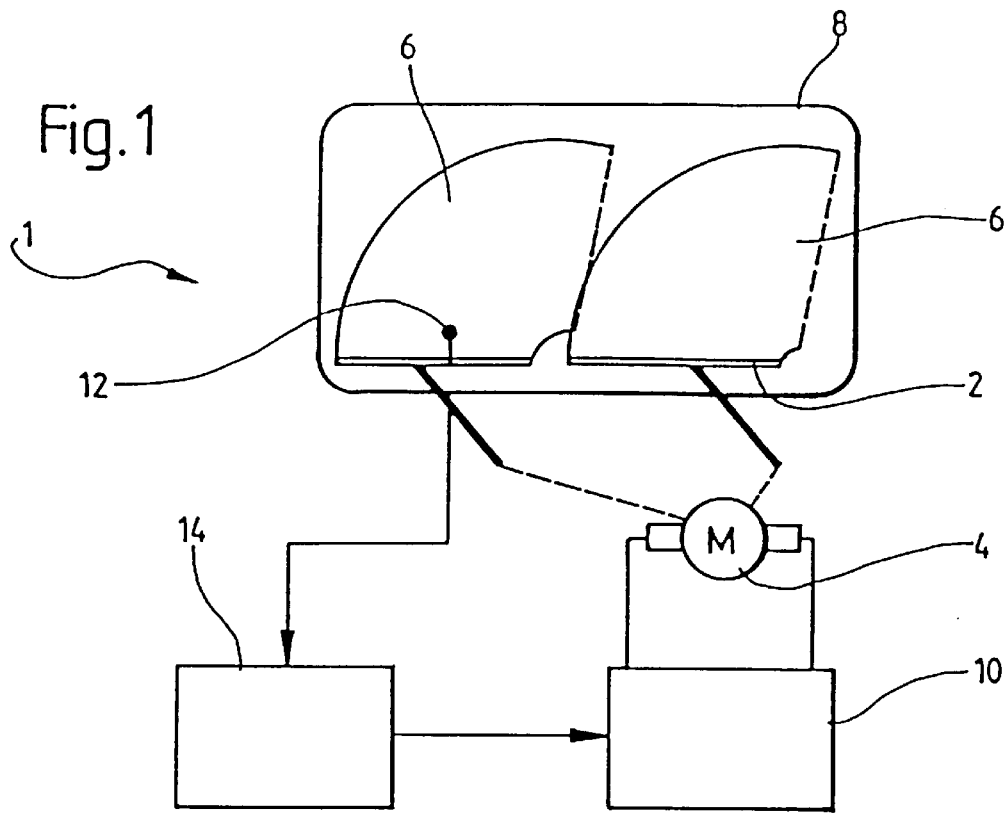
FIG. 1 shows a general schematic diagram of an example of an automatically controlled windscreen cleaning system using a detection device according to the invention.

Referring to FIG. 1, a conventional automatically controlled cleaning system of windscreen wipers designated by the general reference 1 is shown. System 1 comprises windscreen wipers 2 mechanically coupled to a motor 4. When windscreen wipers 2 are activated, they wipe respectively zones 6 which are in the form of a circular sector of a windscreen 8. Activating means 10, connected to motor 4, enable the motor to be switched on and/or off.

The automatic control of the windscreen wipers is achieved with the aid of detection device 12 according to the invention, placed facing one of zones 6. The detection device co-operates with a control circuit 14 capable of providing an appropriate control signal to activating means 10 in response to a detection signal originating from detection device 12.

Figure 2:
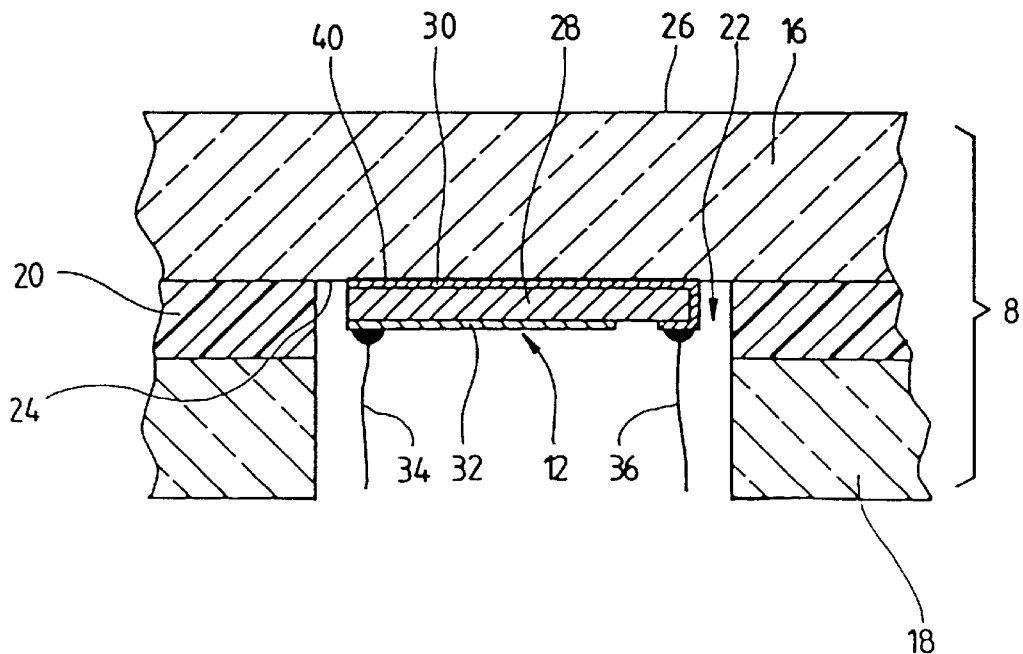
FIG. 2 is a schematic cross-section view of an embodiment of a detection device according to the invention mounted on a motor vehicle windscreen.

Referring now to FIG. 2, there is seen a cross-section of an embodiment of a windscreen in which detection device 12 according to the invention is integrated, such device providing a detection signal representative of the presence of foreign bodies on the exterior surface of windscreen 8 and in particular the presence of rain on the surface of the latter.

Windscreen 8 includes a first sheet 16 and a second sheet 18 joined together by a connecting layer 20. In the example described, sheets 16 and 18 are made of glass, and connecting layer 20 is made of a polymer such as polyvinyl butadiene (PVB).

Detection device 12 is placed, via a recess 22 arranged respectively in sheet 18 and in connecting layer 20, on a face 24 of sheet 16 opposite an exterior face 26 of the same sheet. Face 26 is the face of the windscreen in contact with the foreign bodies to be detected.

Detection device 12 comprises a piezoelectric transducer 28 used successively in transmission and reception mode. Transducer 28 has for example the shape of a disc, which is provided with excitation electrodes 30, 32, insulated from each other and intended to be connected respectively to control circuit 14 via conductors 34, 36.

The operating principle of detection device 12 is as follows.

Control circuit 14 excites piezo-electric transducer 28 by means of a short voltage pulse thus generating a train of ultrasonic waves, the transducer then picking up the multiple echoes reflected respectively by the inner and outer faces of sheet 16. The amplitude of the captive ultrasonic wave of sheet 16 decreases with time, on the one hand, because of the energy lost towards the outside of the sheet upon each reflection and, on the other hand, because of the dissipation of energy in the mass of the sheet.

When there are drops of rain on surface 26, an additional energy is lost during reflection on surface 26, which leads to a more rapid damping in the train of reflected ultrasonic waves.

Figure 3A:
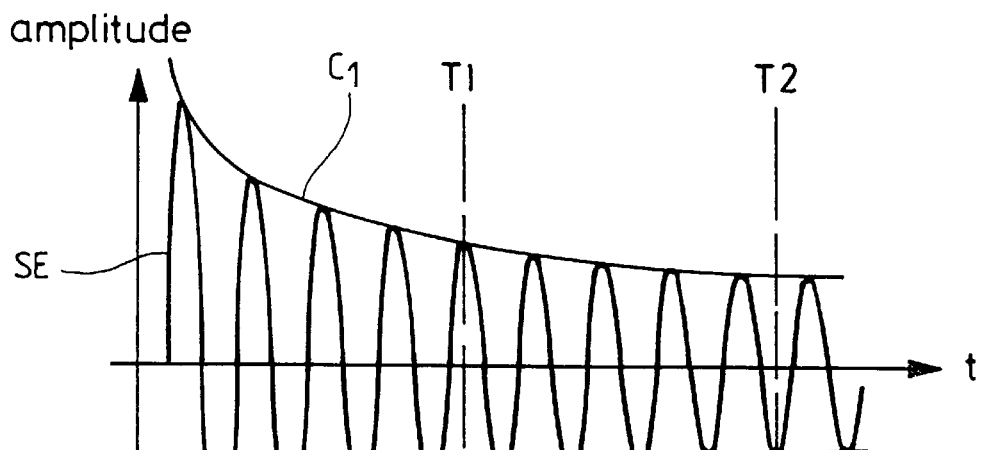
FIGS. 3a and 3b show respectively the shape of an ultrasonic signal after reflection onto a dry and a moist windscreen.
Figure 3B:
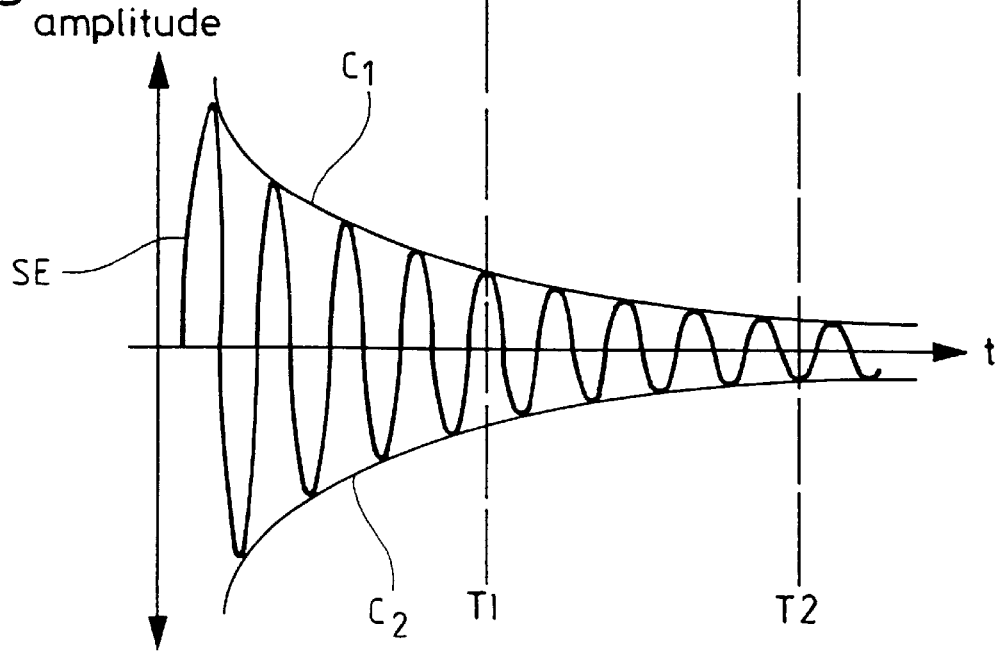

This situation is illustrated in FIGS. 3a and 3b showing respectively the damping in the train of reflected ultrasonic waves when face 26 of sheet 16 is dry (3a) and wet (3b).

By way of indication, the amplitude of the electric excitation pulse is of the order of 10 volts and its duration is approximately 125 nanoseconds. Moreover, the considered temporal domain of the train of damped ultrasonic waves used to determine the presence or absence of water on surface 26, is of the order of several tens of microseconds, typically of between 50 and 80 microseconds.

Control circuit 14 measures integral S corresponding to the surface of the signal echo envelope SE represented by curves C1 and C2 included inside a temporal window which opens at T1 typically twenty microseconds after the excitation pulse and which closes at T2 as has just been mentioned, typically 30 microseconds later.

This integral has a given value in the absence of rain and this value decreases substantially in the presence of water on surface 26, this decrease being in relation to the quantity of water detected by transducer 28.

For proper operation of the detection device, and as it has already been described in patent application EP-A-0 641 696, natural frequency $f_t$ of transducer 28 must be selected to be close to one of the natural frequencies of the resonant cavity formed by sheet 16. In other words, $f_t$ must be substantially equal to $f_K = K \cdot V/2e$, $f_t$ being the resonant frequency of the transducer without stress, i.e. not connected to sheet 16, $f_K$ being the frequency of the kth natural mode of the resonant cavity formed by sheet 16, V being the speed of the ultrasonic wave generated by the transducer in the material forming sheet 20, e being the thickness of said sheet 16 and K being a non zero integral number.

The applicant has found that the notion of ft substantially "equal" to fK must in fact satisfy the following equation:

$$f_K/100 \leq |f_t - f_K| \leq f_K/10, \quad (1)$$

$f_t$ being able to be greater or smaller than $f_K$.

This first equation thus describes two frequency ranges having a width equal to $f_K/10 - f_K/100$, situated symmetrically on either side of the resonant frequency corresponding to the Kth natural vibration mode of the sheet of thickness e. These two preferred ranges are represented in FIG. 4 which shows a curve C illustrating in arbitrary units the evolution of sensitivity to a drop of water whose surface in contact with face 26 of the windscreen as a function of the frequency difference $f_t - f_K$. Sensitivity means the variation in signal $S = \int Env(t) \, dt$ corresponding to the variation in the surface of the envelope of the train of reflected ultrasonic waves between T1 and T2 (FIGS. 3a, 3b) when the windscreen is dry or damp due to a drop of water whose surface in contact with face 26 of the windscreen is determined precisely. It is to be noted that curve C comprises two distinct regions R1 and R2 defining the ranges of good sensitivity of the detection device according to the invention and according to equation (1).

It has also been noted that even more satisfactory results may be obtained when transducer frequency $f_t$ is selected to satisfy the following equation:

$$f_K/100 \leq f_t - f_K \leq f_K/10 \quad (2)$$

with $f_t$ greater than $f_K$, which corresponds to the range to the left of FIG. 4.

By way of example, for a sheet 18 having a thickness of $2.59 \times 10^{-3}$ m, a value V of 5880 m.s$^{-1}$ and a selected value K=4, a value $f_K$=4,527 MHz is obtained. Thus the difference $|f_t - f_K|$ may be of between 0.045 and 0.45 MHz according to equation (1). It will be noted that in an advantageous manner particularly satisfactory results are obtained by selecting integral numbers 3 or 4 as values of K.

In FIG. 2, a preferred means for coupling transducer 28 to face 24 of sheet 16 is shown. In this example, transducer 28 is fixed by means of a film of glue 40 allowing the transmission of ultrasonic waves from transducer 28 to sheet 16. It is to be noted however in this regard that the coupling film has a very small thickness with respect to the wavelength λ of the signal emitted by the transducer, in order to avoid too great an absorption of the ultrasonic signal. The applicant has confirmed that typically the use of a coupling film having a thickness of between 10 and 30 μm leads to satisfactory results.

By way of example, the coupling means may include a glue or a silicon oil.

In order to achieve uniform and efficient transmission and reception of the ultrasonic signals emitted and received by the transducer, care should be taken that no air bubbles are present at the interfaces transmitting the signals.

It will also be noted that in the event that transducer 28 is fixed onto a sheet formed of a sandwich, for example comprising several sheets of glass, thickness e indicated in the aforementioned equations will correspond to the equivalent thickness of the sandwich and $f_K$ will correspond to the resonant frequency of the sandwich or to a multiple of such frequency. In other words, the first sheet mentioned in the claims may comprise several assembled sheets of glass having an equivalent thickness.

What is claimed is:

1. An ultrasonic detection device intended to detect the presence of foreign bodes, in particular moist bodies, present on the surface of a window comprising at least a first sheet having a first thickness, the device comprising a transducer co-operating with a first face of said first sheet, said transducer being able to emit, an ultrasonic signal of frequency $f_t$ and able to receive a reflected ultrasonic signal on a second face of the first sheet, the variation in said reflected signal being representative of the presence or absence of foreign bodies on said second face facing said transducer, wherein the frequency $f_t$ is selected to satisfy the following equation:

$$f_K/100 \leq |f_t - f_K| \leq f_K/10$$

where $f_K = K \cdot V/2e$ is the frequency of the Kth natural mode of the resonant cavity formed by the first sheet of glass, K being a non zero integral number, V the speed of propagation of the ultrasonic wave in the material forming the first sheet and e the thickness of the first sheet.

2. A detection device according to claim 1, wherein the frequency ft is selected to satisfy the following equation:

$$f_K/100 \leq f_t - f_K \leq f_K/10$$

$f_t$ being greater than $f_K$.

3. A detection device according to claim 1, wherein the value of K is equal to 3 or 4.

4. A detection device according to claim 2, wherein the value of K is equal to 3 or 4.

* * * * *